United States Patent [19]
Luther et al.

[11] Patent Number: 5,980,872
[45] Date of Patent: Nov. 9, 1999

[54] SUNSCREEN COMPOSITIONS

[75] Inventors: Helmut Luther, Grenzach-Wyhlen, Germany; Albert Stehlin, Rosenau, France; Marina Minklei, Grenzach, Germany

[73] Assignee: Ciba Specialty Chemicals Corporation, Tarrytown, N.Y.

[21] Appl. No.: 09/000,026

[22] PCT Filed: Jul. 11, 1996

[86] PCT No.: PCT/EP96/03044

§ 371 Date: Apr. 20, 1998

§ 102(e) Date: Apr. 20, 1998

[87] PCT Pub. No.: WO97/03643

PCT Pub. Date: Feb. 6, 1997

[30] Foreign Application Priority Data

Jul. 22, 1995 [GB] United Kingdom .................. 9515048

[51] Int. Cl.⁶ .............................. A61K 7/42; A61K 7/44; A61K 7/00; A61K 9/14
[52] U.S. Cl. .............................. 424/59; 424/60; 424/401; 424/489; 514/844; 514/937; 514/944; 514/951
[58] Field of Search .................................... 424/401, 489, 424/59, 60; 514/844, 937, 944, 951

[56] References Cited

U.S. PATENT DOCUMENTS 4,617,390 10/1986 Hoppe et al. ........................... 544/197
5,631,215 5/1997 Kinsman ................................. 510/130

FOREIGN PATENT DOCUMENTS 2 286 774 8/1995 United Kingdom .
2286774 8/1995 United Kingdom .

OTHER PUBLICATIONS

Electro Chemistry in Colloids and Dispersion, 399ff.

*Primary Examiner*—Shelley A. Dodson
*Assistant Examiner*—Marina Lamm
*Attorney, Agent, or Firm*—Kevin T. Mansfield; Luther A. R. Hall

[57] ABSTRACT

The present invention provides a method of producing a composition, suitable for use in pharmaceutical or cosmetic compositions, comprising a micronised insoluble organic UV absorber, which method comprises grinding the insoluble organic UV absorber, in coarse particle form, in a grinding apparatus, in the presence of 0.1 to 30% by weight of an alkyl polyglucoside having the formula $C_nH_{2n+1}O(C_6H_{10}O_5)_xH$, in which n is an integer ranging from 8 to 16 and x is the mean polymerization level of the glucoside moiety $(C_6H_{10}O_5)$ and ranges from 1.4 to 1.6, or an ester thereof.

38 Claims, No Drawings

SUNSCREEN COMPOSITIONS

The present invention relates to a method for producing new formulations of UV absorbers and to their use in sunscreen compositions which, in turn, are useful, in particular, for the protection of human skin.

It has long been known that prolonged exposure to that UV radiation which reaches the surface of the earth can lead to the formation of erythemas or light dermatoses, as well as to an increased incidence of skin cancers or accelerated skin aging.

Various sunscreen formulations have been proposed which include a material which is intended to counteract UV radiation, thereby inhibiting the said undesired effects on the skin.

A great number of compounds has been proposed for use as UV protectants in sunscreen formulations, especially soluble organic UV absorbers and insoluble micronised inorganic compounds, in particular zinc oxide and titanium dioxide.

With respect to the use in sunscreen formulations of soluble organic UV absorbers, they have the disadvantages that their effectiveness as UV protectants in terms of SPF (Sun Protection Factor) in a sunscreen formulation is often too low for commercial purposes; as a result of their solubility, they exhibit relatively high allergenic potential; and that as a result of intrinsic photochemical lability, the duration of the protective effect is often too low.

The high specific weight of insoluble inorganic compounds, such as zinc oxide and titanium dioxide leads to a reduced stability of formulations containing them. Moreover, such inorganic compounds have been claimed to generate toxic radicals under the influence of light ("Redox Mechanisms in Heterogeneous Photocatalysis", Serpone et al, Electrochemistry in Colloids and Dispersions, Editors Mackay and Texter, VCH Publishers Inc., New York 1992).

Micronized, insoluble organic UV absorbers, when used in sunscreen formulations, provide excellent UV protection and have at least as high an SPF rating as corresponding sunscreen formulations containing a known inorganic UV absorber. Unlike the latter UV absorbers, micronized, insoluble organic UV absorbers show no tendency, under the influence of light, to generate radicals which could damage or sensitise human skin.

Accordingly, the present invention provides, as a first aspect, a method of producing a composition, which is especially suitable for use in pharmaceutical or cosmetic applications, comprising a micronised insoluble organic UV absorber, which method comprises grinding the insoluble organic UV absorber, in coarse particle form, in a grinding apparatus, in the presence of 1 to 50%, preferably 5 to 40% by weight, based on the micronised insoluble organic UV absorber, of an alkyl polyglucoside having the formula $C_nH_{2n+1}O(C_6H_{10}O_5)_xH$, in which n is an integer ranging from 8 to 16 and x is the mean polymerisation level of the glucoside moiety $(C_6H_{10}O_5)$ and ranges from 1.4 to 1.6, or an ester thereof.

The insoluble organic UV absorber may be, e.g., an oxanilide, a triazine, a triazole, a vinyl group-containing amide, a cinnamic acid amide or a sulfonated benzimidazole UV absorber.

One preferred class of oxanilide UV absorbers is that having the formula:

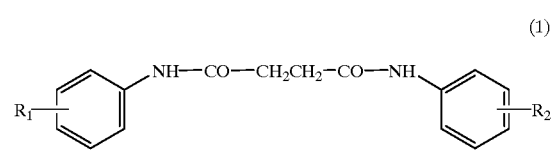

(1)

in which $R_1$ and $R_2$, independently, are $C_1$–$C_{18}$alkyl or $C_1$–$C_{18}$alkoxy. A preferred compound of formula (1) is N-(2-ethoxyphenyl)-N'-(2-ethylphenyl)-ethanediamide.

A preferred class of triazine compounds is that having the formula:

(2)

in which $R_3$, $R_4$ and $R_5$, independently, are H, OH, $C_1$–$C_{18}$alkoxy, $NH_2$, NH—$R_6$ or $N(R_6)_2$ in which $R_6$ is $C_1$–$C_{18}$alkyl, $OR_6$ in which $R_6$ has its previous significance, phenyl, phenoxy or anilino, or pyrrole, in which the respective phenyl, phenoxy or anilino, or pyrrolo moieties are optionally substituted by one, two or three substitutents selected from OH, carboxy, CO—$NH_2$, $C_1$–$C_{18}$alkyl or -alkoxy, $C_1$–$C_{18}$carboxyalkyl, $C_5$–$C_8$cycloalkyl, a methylidenecamphor group, a group —(CH=CH)$_m$C(=O)—$OR_6$ in which m is 0 or 1 and $R_6$ has its previous significance, or a group

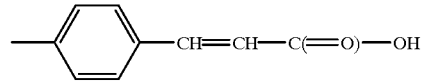

or the corresponding alkali metal, ammonium, mono-, di- or tri-$C_1$–$C_4$alkylammonium, mono-, di- or tri-$C_2$–$C_4$alkanolammonium salts, or the $C_1$–$C_{18}$alkyl esters thereof.

Preferred compounds of formula (2) are those having one of the formulae:

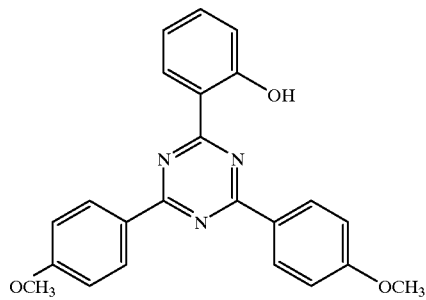
(3)
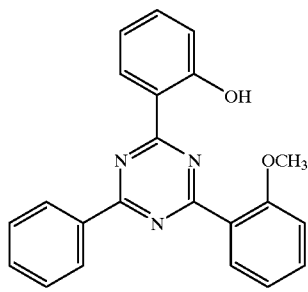
(4)
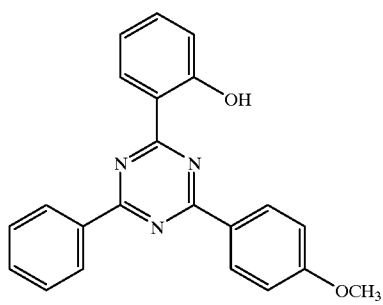
(5)
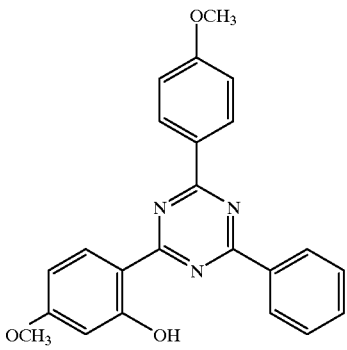
(6)
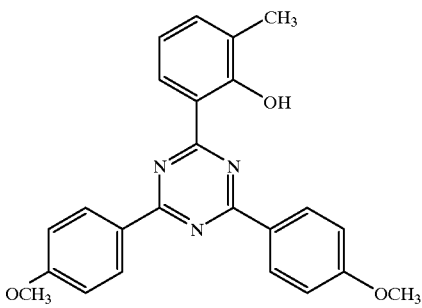
(7)

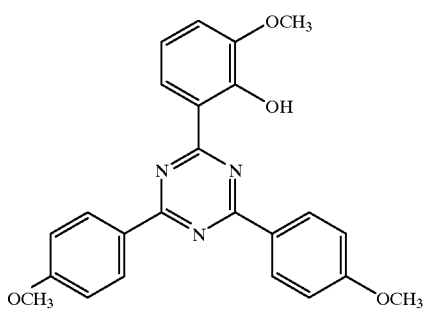
(8)
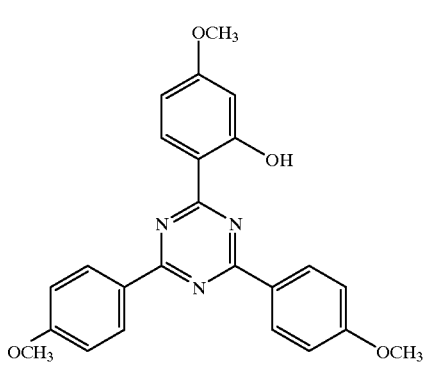
(9)
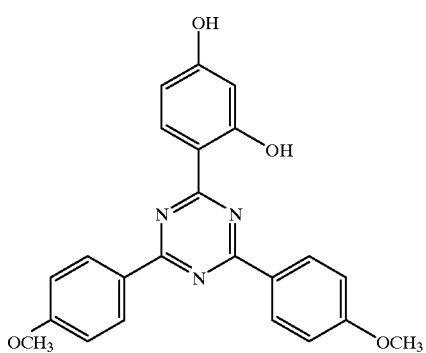
(10)
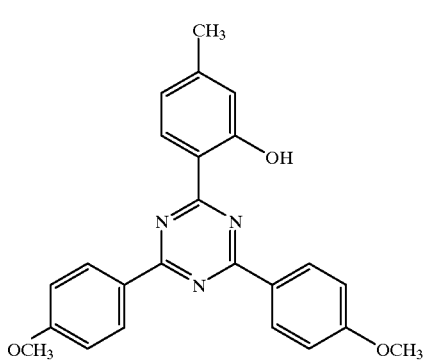
(11)

-continued
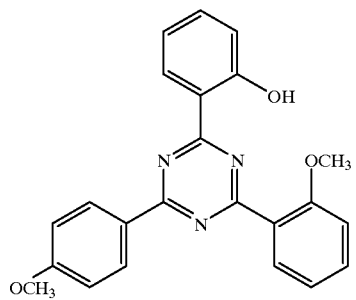
(12)
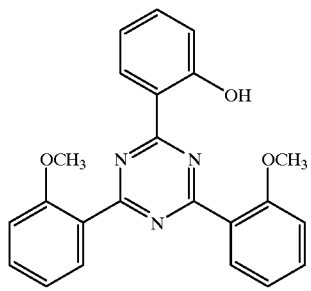
(13)
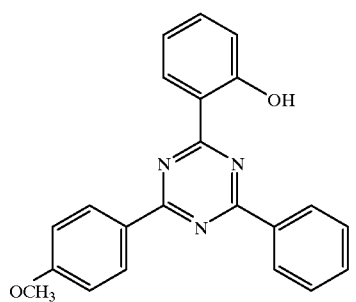
(14)
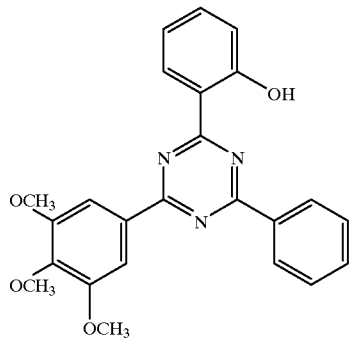
(15)
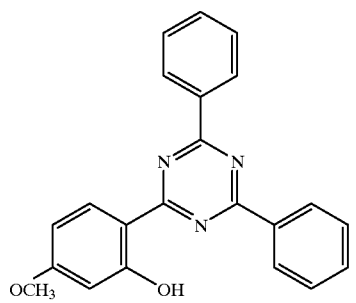
(16)

-continued
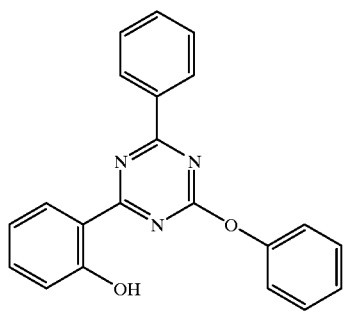
(17)
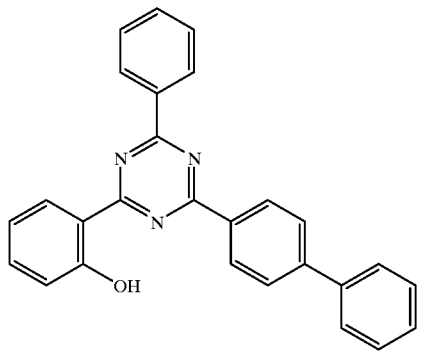
(18)
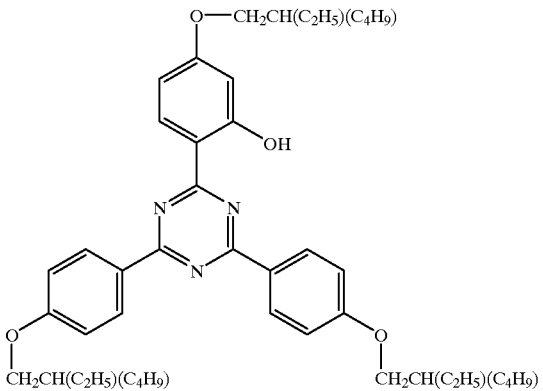
(19)
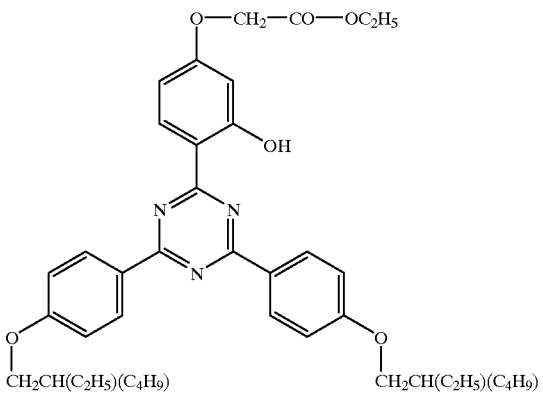
(20)

-continued
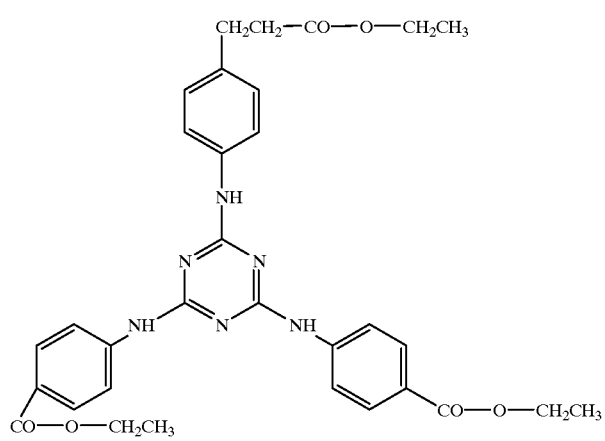
(21)
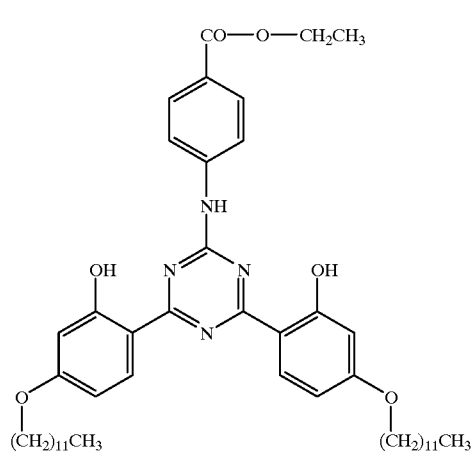
(22)
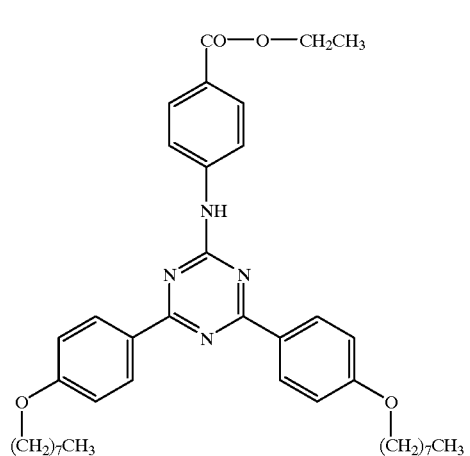
(23)

-continued
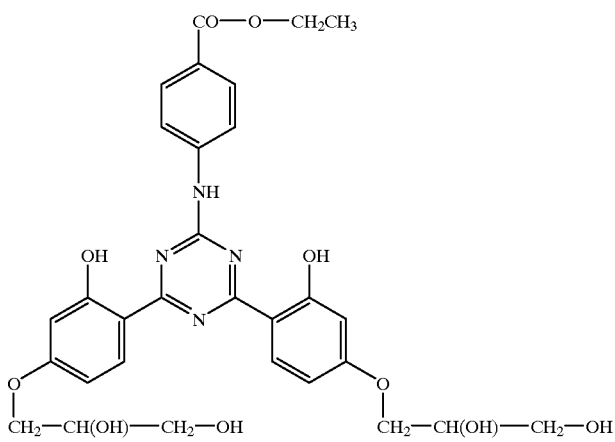
(24)
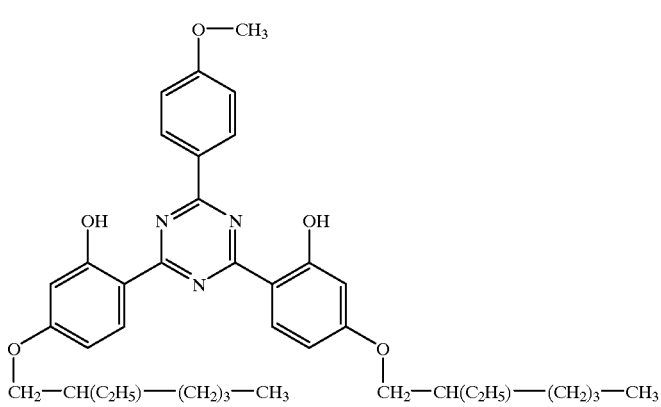
(25)
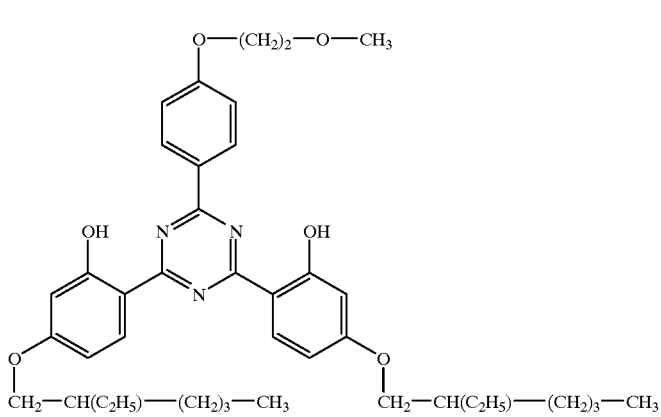
(26)
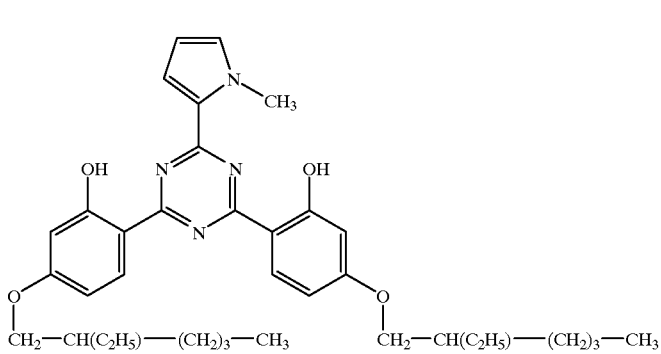
(27)

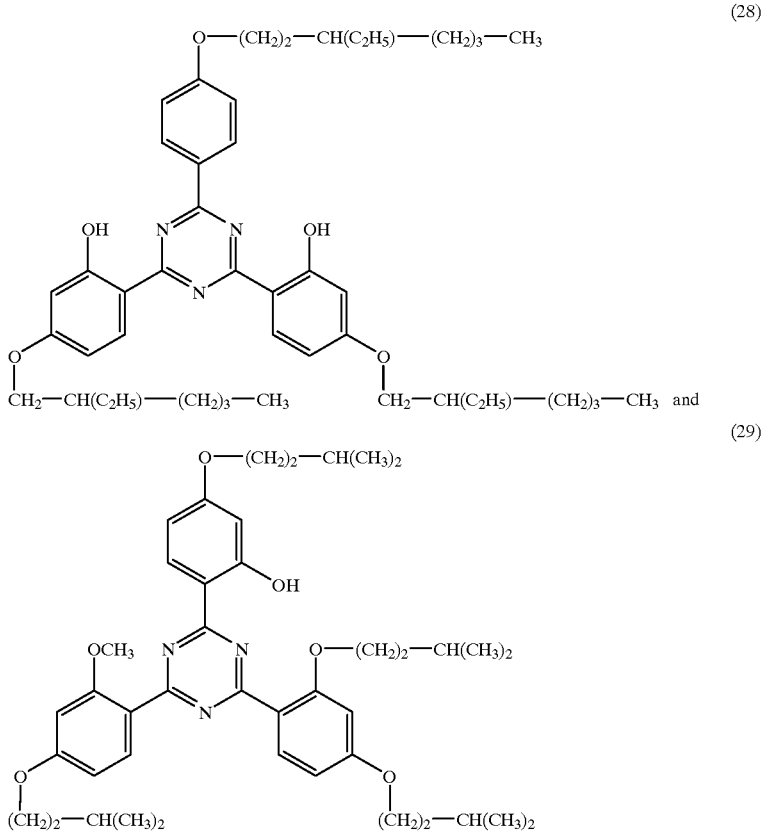

(28)

(29)

as well as 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine.

Particularly preferred compounds of formula (2) are those having the formula:

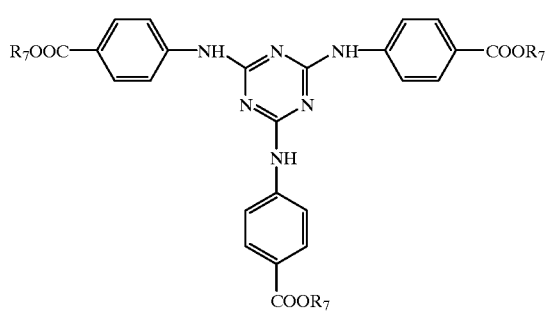

(30)

in which the individual radicals $R_7$ are the same or different and each is hydrogen; an alkali metal; an ammonium group $N(R_8)_4$ in which $R_8$ is hydrogen or an organic radical; $C_1$–$C_{20}$alkyl; or a polyoxyethylene radical which contains from 1 to 10 ethylene oxide units and the terminal OH group of which may be etherified by a $C_1$–$C_3$alcohol.

In relation to the compounds of formula (30), when $R_7$ is an alkali metal it is preferably potassium or, especially sodium; when $R_7$ is a group $N(R_8)_4$ in which $R_8$ has its previous significance, it is preferably a mono-, di- or tri-$C_1$–$C_4$alkylammonium salt, a mono-, di- or tri-$C_2$–$C_4$alkanolammonium salt or a $C_1$–$C_{20}$alkyl ester thereof; when $R_8$ is a $C_1$–$C_{20}$alkyl group, it is preferably a $C_6$–$C_{12}$alkyl group, more preferably a $C_8$–$C_9$alkyl group, especially the 3,5,5-trimethylpentyl group or, most particularly, the 2-ethylhexyl group; and when $R_8$ is polyoxyethylene group, this preferably contains from 2–6 ethylene oxide units.

One preferred class of triazole insoluble organic UV absorbers is that having the formula:

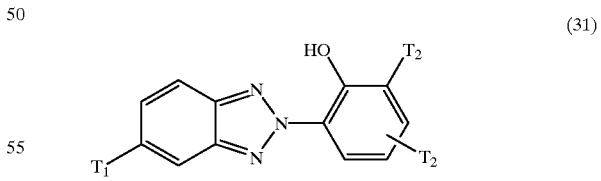

(31)

in which $T_1$ is $C_1$–$C_{18}$alkyl or, preferably, hydrogen; and $T_2$ is $C_1$–$C_{18}$alkyl, optionally substituted by phenyl, preferably α,α-dimethylbenzyl.

A further preferred class of triazole insoluble organic UV absorbers is that having the formula:

(32)

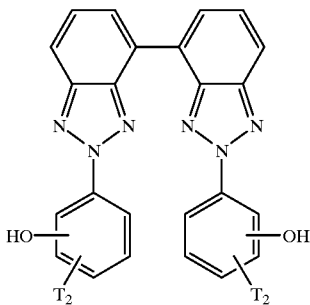

in which T₂ has its previous significance.

A still further preferred class of triazole insoluble organic UV absorbers is that having the formula:

(33)

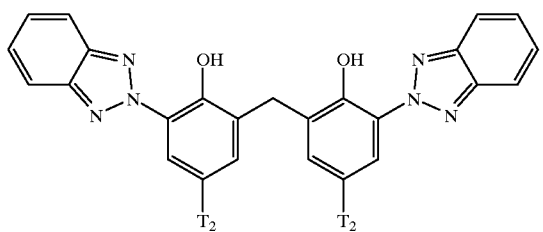

in which T₂ has its previous significance and is preferably t-butyl.

A preferred class of vinyl group-containing amide insoluble organic UV absorbers is that having the formula:

$R_9-(Y)_m-CO-C(R_{10})=C(R_{11})-N(R_{12})(R_{13})$ (34)

in which $R_9$ is $C_1-C_{18}$alkyl, preferably $C_1-C_5$alkyl, or phenyl optionally substituted by one, two or three substituents selected from OH, $C_1-C_{18}$alkyl, $C_1-C_{18}$alkoxy or CO—$OR_6$ in which $R_6$ has its previous significance; $R_{10}$, $R_{11}$, $R_{12}$ and $R_{13}$ are the same or different and each is $C_1-C_{18}$alkyl, preferably $C_1-C_5$alkyl, or hydrogen; Y is N or O; and m has its previous significance.

Preferred compounds of formula (34) are 4-octyl-3-penten-2-one, ethyl-3-octylamino-2-butenoate, 3-octylamino-1-phenyl-2-buten-1-one and 3-dodecylamino-1-phenyl-2-buten-1-one.

A preferred class of cinnamic acid amide insoluble organic UV absorbers is that having the formula:

(35)

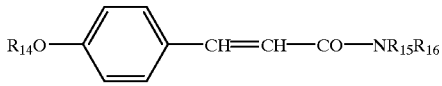

in which $R_{14}$ is hydroxy or $C_1-C_4$alkoxy, preferably methoxy or ethoxy; $R_{15}$ is hydrogen or $C_1-C_4$alkyl, preferably methyl or ethyl; and $R_{16}$ is —(CONH)$_m$-phenyl in which m has its previous significance and the phenyl group is optionally substituted by one, two or three substituents selected from OH, $C_1-C_{18}$alkyl, $C_1-C_{18}$alkoxy or CO—$OR_6$ in which $R_6$ has its previous significance. Preferably $R_{16}$ is phenyl, 4-methoxyphenyl or the phenylaminocarbonyl group.

A preferred class of sulfonated benzimidazole insoluble organic UV absorbers is that having the formula:

(36)

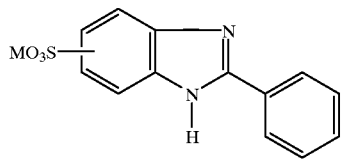

in which M is hydrogen or an alkali metal, preferably sodium, an alkaline earth metal, such as magnesium or calcium, or zinc.

In the compounds of formula (1) to (35), $C_1-C_{18}$alkyl groups may be methyl, ethyl, n-propyl, isopropyl, n-butyl, isobutyl, tert-butyl, n-amyl, n-hexyl, n-heptyl, n-octyl, isooctyl, n-nonyl, n-decyl, n-undecyl, n-dodecyl, tetradecyl, hexydecyl or octadecyl; and $C_1-C_{18}$alkoxy groups include methoxy, ethoxy, propoxy, butoxy, n-hexoxy, n-heptoxy, n-octoxy, isooctoxy, n-nonoxy, n-decoxy, n-undecoxy, n-dodecoxy, tetradecoxy, hexadecoxy or octadecoxy, methoxy and ethoxy being preferred.

$C_1-C_{18}$carboxyalkyl includes carboxymethyl, carboxyethyl, carboxypropyl, carboxyisopropyl, carboxybutyl, carboxyisobutyl, carboxybutyl, carboxyamyl, carboxyhexyl, carboxyheptyl, carboxyoctyl, carboxyisooctyl, carboxynonyl, carboxydecyl, carboxyundecyl, carboxydodecyl, carboxytetradecyl, carboxyhexadecyl and carboxyoctadecyl, carboxymethyl being preferred.

$C_5-C_8$cycloalkyl includes cyclopentyl, cyclohexyl and cyclooctyl.

The compounds of formula (1) to (35) are known. The compounds of formula (30) are described, together with their production, in U.S. Pat. No. 4,617,390.

Although they are excellent sun screen agents per se, the insoluble organic UV absorbers suffer from the drawback that, to date, it has proved difficult to formulate them in order to achieve a high SPF in human sun screen applications.

Surprisingly, it has now been found that the insoluble organic UV absorbers, when micronised with a particular type of surfactant, namely an alkyl polyglucoside, provide high SPF values. Moreover, such formulations do not agglomerate and they remain in a dispersed form and do not readily settle.

Preferably, the micronised insoluble organic UV absorber, produced according to the method of the present invention, has a mean particle size in the range of from 0.01 to 2, more preferably from 0.02 to 1.5, especially from 0.05 to 1.0μ.

The grinding apparatus used to conduct the method of the present invention may be, e.g., a jet, ball, vibration or hammer mill, preferably a high speed stirring mill or impact mill, especially a rotating ball mill, vibrating mill, tube mill or rod mill.

The alkyl polyglucoside may consist of a $C_1-C_{12}$ester of the compound of formula $C_nH_{2n+1}O(C_6H_{10}O_5)_xH$, namely an ester formed by reacting a $C_1-C_{12}$acid, such formic, acetic, propionic, butyric, sulfosuccinic, citric or tartaric acid, with one or more free OH groups on the glucoside moiety ($C_6H_{10}O_5$).

The micronised formulation of a insoluble organic UV absorber, produced according to the method of the present invention may be used together with one or more further UV absorbers, such as soluble organic UV absorbers, insoluble inorganic UV absorbers and/or melanine, which are conventionally used in cosmetic compositions for the protection of human skin against UV radiation. The use of such combinations of active ingredients may lead to synergistic effects.

As already indicated, the composition produced according to the method of the present invention is particularly suitable for use in a sunscreen formulation.

Accordingly, the present invention also provides a sunscreen composition comprising a) 0.1 to 15%, preferably 0.5 to 10% by weight, based on the total composition of a micronised formulation of an insoluble organic UV absorber, produced according to the method of the present invention; and optionally b) a cosmetically acceptable carrier.

The sunscreen composition of the present invention may be produced by physically blending the micronised formulation of an insoluble organic UV absorber and carrier components by any conventional method, e.g. by simply stirring the two materials together. In a preferred procedure, a mixture of the coarse, insoluble organic UV absorber, the alkyl polyglucoside grinding aid, and the milling bodies are ground until the coarse, insoluble organic UV absorber has been converted into micronised form, as described earlier in relation to the production of the micronised insoluble organic UV absorber. After filtering off the milling bodies, e.g. quartz sand, glass balls or zirconium silicate balls, the filtrate, consisting of the micronised insoluble organic UV absorber and grinding aid components, may be blended with a cosmetically compatible carrier.

The sunscreen composition of the invention may be formulated as a water-in oil or an oil-in-water dispersion, an oil or oil-alcohol lotion, a vesicular dispersion of an ionic or nonionic amphiphilic lipid, a gel, a solid stick or an aerosol formulation.

When formulated as a water-in oil or an oil-in-water dispersion, the optional cosmetically acceptable carrier preferably comprises 5 to 50% of an oil phase, 5 to 20% of an emulsifier and 30 to 90% of water, each by weight based on the total weight of the carrier.

The oil phase may comprise any oil conventionally used in cosmetic formulations, e.g., one or more of a hydrocarbon oil, a wax, a natural oil, a silicone oil, a fatty acid ester or a fatty alcohol. Preferred mono- or polyols are ethanol, isopropanol, propylene glycol, hexylene glycol, glycerine and sorbitol.

The emulsifier also may comprise any emulsifier conventionally used in cosmetic formulations, e.g., one or more of an ethoxylated ester of a natural oil derivative such as a polyethoxylated ester of hydrogenated castor oil; a silicone oil emulsifier such as a silicone polyol; an optionally ethoxylated fatty acid soap; an ethoxylated fatty alcohol; an optionally ethoxylated sorbitan ester; an ethoxylated fatty acid; or an ethoxylated glyceride.

The sunscreen composition of the invention may also comprise further components which are known to perform a useful function in a sunscreen composition. Examples of such further components include, e.g., emollients, skin moisturisers, skin tanning accelerators, antioxidants, emulsion stabilisers, thickening agents such as xanthan, moisture-retention agents such as glycerine, film formers, preservatives, perfumes and colourants.

The sunscreen composition of the invention provides excellent protection of the human against the damaging effects of sunlight, while permitting safe tanning of the skin. Moreover, the sunscreen composition of the invention has a skin waterproofing effect.

The following Examples further illustrate the present invention.

EXAMPLE 1

30 g of 2,4,6-trianilino-p-(carbo-2'-ethylhexyl-1'-oxy)-1,3,5-triazine having the formula:

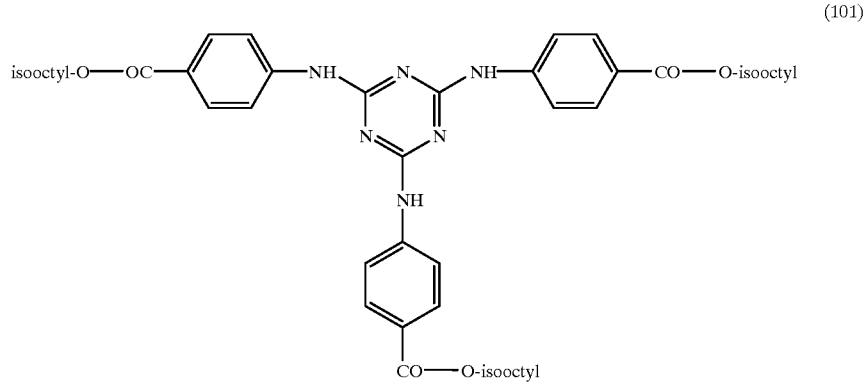

(101)

are ground in a 200 ml grinding container at a stirring speed of 8 m/s in a Drais bead mill in the presence of 12 g of a $C_8$–$C_{16}$ fatty alcohol polyglucoside and 300 g of zirconium silicate grinding aids (diameter 0.6–0.8 mm), over 15 minutes, with water cooling. The grinding aids are centrifuged off and the mean particle size of the remaining dispersion product is found to be 1.06$\mu$ (measured on a Malvern Mastersizer).

5 g of the resulting dispersion are then formulated with 0.25 g NaCl, 0.25 g of a polydimethylsiloxane de-foamer, 13.25 g of water and 6.25 g of a thickener which contains, per litre, 16 g imidazolidinyl urea, 24 g of a mixture of methyl-, ethyl-, i-butyl- and n-butyl esters of 4-hydroxybenzoic acid in phenoxyethanol, 40 g xanthan gum and 940 g water.

The resulting lotion formulation is composed of:
10.0% 2,4,6-trianilino-p-(carbo-2'-ethylhexyl-1'-oxy)-1,3,5-triazine;
8.0% $C_8$–$C_{16}$ fatty alcohol polyglucoside;
78.5% water;
1.0% de-foamer;
1.0% NaCl;
0.5% xanthan gum;
0.5% imidazolidinyl urea; and
0.6% mixed esters of 4-hydroxybenzoic acid.

The lotion has an average SPF (measured on an SPF analyzer/Optometrics according to DIN 67501) of 13.2.

EXAMPLE 2

Using an analogous procedure to that described in Example 1 but applying a grinding time of 30 minutes, a formulation is obtained having a mean particle size of 0.9μ (measured on a Malvern Mastersizer) and an average SPF of 19.5.

EXAMPLE 3

Using an analogous procedure to that described in Example 1 but applying a grinding time of 45 minutes, a formulation is obtained having a mean particle size of 0.88μ (measured on a Malvern Mastersizer) and an average SPF of 22.8.

EXAMPLE 4

Using an analogous procedure to that described in Example 1 but applying a grinding time of 80 minutes, a formulation is obtained having a mean particle size of 0.73μ (measured on a Malvern Mastersizer) and an average SPF of 33.7.

The dependence of SPF on the level of micronisation is clearly apparent from the data in Examples 1 to 4.

EXAMPLE 5

Using the procedure described in Example 1, but replacing the 2,4,6-trianilino-p-(carbo-2'-ethylhexyl-1'-oxy)-1,3,5-triazine used therein by the compound having the formula:

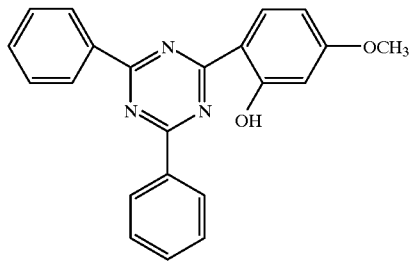

(102)

there is obtained a lotion formulation which is composed of:
10.0% compound (102);
4.0% $C_8$–$C_{16}$ fatty alcohol polyglucoside;
82.5% water;
1.0% de-foamer;
1.0% NaCl;
0.5% xanthan gum;
0.5% imidazolidinyl urea; and
0.6% mixed esters of 4-hydroxybenzoic acid.

The lotion has an average SPF (measured on an SPF analyzer/Optometrics according to DIN 67501) of 18.7 at a particle size of 0.22μ.

Similar results are obtained using a lotion formulation which is composed of:
10.0% compound (102);
4.0% $C_8$–$C_{16}$ fatty alcohol polyglucoside;
71.7% water;
1.0% de-foamer;
1.0% propyleneglycolstearate;
5% paraffin oil;
1.5% stearic acid;
0.4% cetyl/stearyl alcohol;
0.1% propyl ester of 4-hydroxybenzoic acid;
0.1% methyl ester of 4-hydroxybenzoic acid;
4.0% glycerine;
0.1% polyacrylic acid;
0.8% triethanolamine; and
0.5% xanthan gum.

EXAMPLE 6

Using the procedure described in Example 5, but replacing the compound of formula (102) used therein by the compound having the formula:

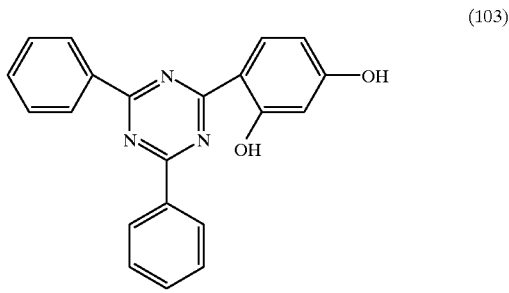

(103)

there is obtained a lotion formulation which has an average SPF (measured on an SPF analyzer/Optometrics according to DIN 67501) of 31 at a particle size of 0.29μ.

EXAMPLE 7

Using the procedure described in Example 5, but replacing the compound of formula (102) used therein by the compound having the formula:

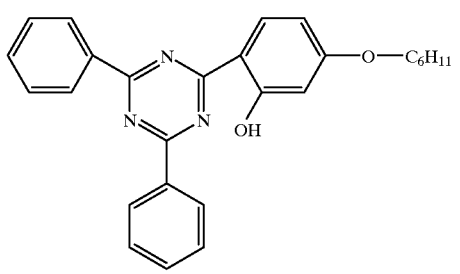

(104)

there is obtained a lotion formulation which has an average SPF (measured on an SPF analyzer/Optometrics according to DIN 67501) of 17.5 at a particle size of 0.44μ.

EXAMPLE 8

Using the procedure described in Example 5, but replacing the compound of formula (102) used therein by the compound having the formula:

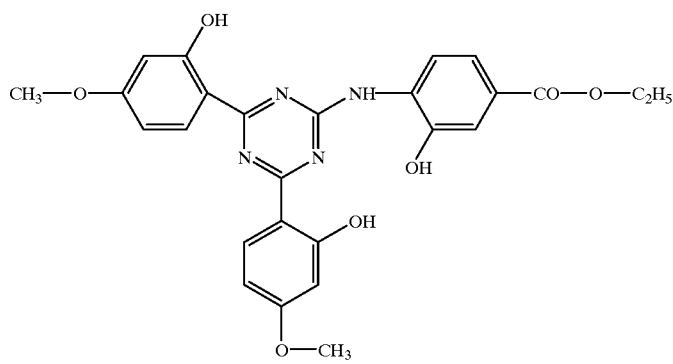

(105)

there is obtained a lotion formulation which has an average SPF (measured on an SPF analyzer/Optometrics according to DIN 67501) of 20.4 at a particle size of 0.4μ.

EXAMPLE 9

Using the procedure described in Example 5, but replacing the compound of formula (102) used therein by the compound having the formula:

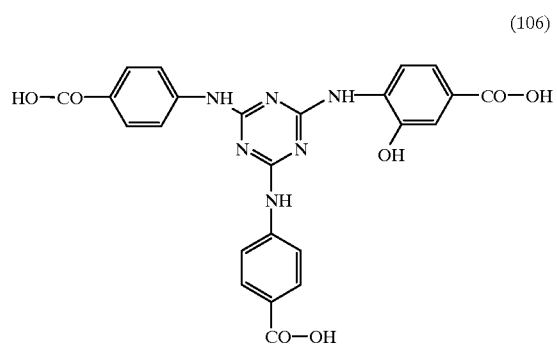

(106)

there is obtained a lotion formulation which has an average SPF (measured on an SPF analyzer/Optometrics according to DIN 67501) of 15.2 at a particle size of 0.32μ.

Similar results are obtained when the acidic compound of formula (106) is replaced by an alkaline earth salt thereof, such as the magnesium or calcium salt, or by the zinc salt thereof.

EXAMPLE 10

Using the procedure described in Example 5, but replacing the compound of formula (102) used therein by the compound having the formula:

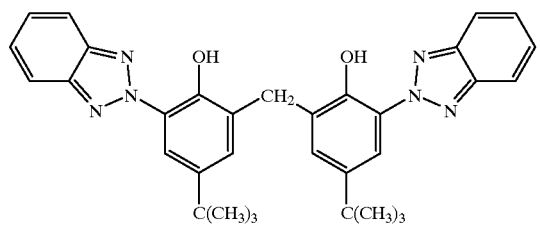

(107)

there is obtained a lotion formulation which has an average SPF (measured on an SPF analyzer/Optometrics according to DIN 67501) of 23.3 at a particle size of 0.43μ.

EXAMPLE 11

Using the procedure described in Example 5, but replacing the compound of formula (102) used therein by the compound having the formula:

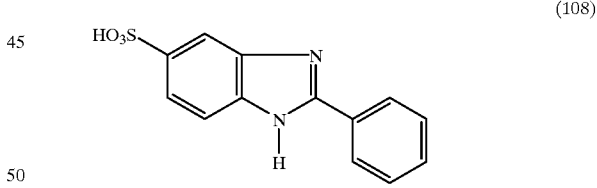

(108)

there is obtained a lotion formulation which has an average SPF (measured on an SPF analyzer/Optometrics according to DIN 67501) of 5.6 at a particle size of 0.4μ.

Similar results are obtained when the acidic compound of formula (108) is replaced by an alkaline earth salt thereof, such as the magnesium or calcium salt, or by the zinc salt thereof.

EXAMPLE 12

Using the procedure described in Example 5, but replacing the compound of formula (102) used therein by the compound having the formula:

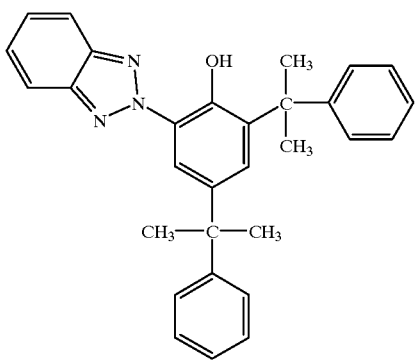

(109)

there is obtained a lotion formulation which has an average SPF (measured on an SPF analyzer/Optometrics according to DIN 67501) of 17.0 at a particle size of 0.31μ.

EXAMPLE 13

Using the procedure described in Example 5, but replacing the compound of formula (102) used therein by the compound having the formula:

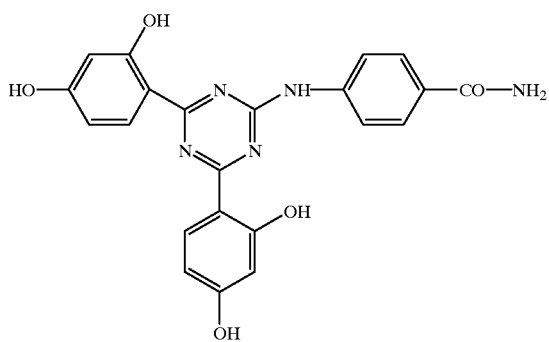

(110)

there is obtained a lotion formulation.

EXAMPLE 14

Using the procedure described in Example 5, but replacing the compound of formula (102) used therein by the compound having the formula:

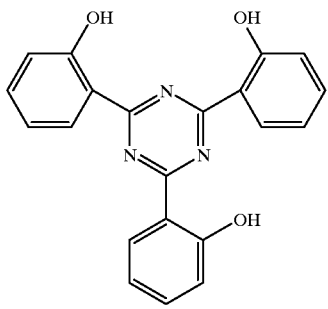

(111)

there is obtained a lotion formulation.

We claim:

1. A method of producing a composition, suitable for use in pharmaceutical or cosmetic compositions, comprising a micronised insoluble organic UV absorber, which method comprises grinding the insoluble organic UV absorber, in coarse particle form, in a grinding apparatus, in the presence of 1 to 50% by weight of an alkyl polyglucoside having the formula $C_nH_{2n+1}O(C_6H_{10}O_5)_xH$, in which n is an integer ranging from 8 to 16 and x is the mean polymerisation level of the glucoside moiety ($C_6H_{10}O_5$) and ranges from 1.4 to 1.6, or an ester thereof.

2. A method according to claim 1 in which the amount of alkyl polyglucoside is from 5 to 40% by weight.

3. A method according to claim 1 in which the insoluble organic UV absorber is an oxanilide, a triazine, a triazole, a vinyl group-containing amide, a cinnamic acid amide or a sulfonated benzimidazole UV absorber.

4. A method according to claim 3 in which the oxanilide UV absorber has the formula:

(1)

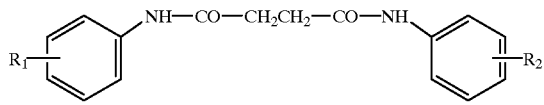

in which $R_1$ and $R_2$, independently, are $C_1$–$C_{18}$alkyl or $C_1$–$C_{18}$alkoxy.

5. A method according to claim 4 in which the compound of formula (1) is N-(2-ethoxyphenyl)-N'-(2-ethylphenyl)-ethanediamide.

6. A method according to claim 3 in which the triazine UV absorber has the formula:

(2)

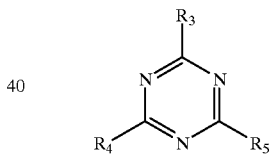

in which $R_3$, $R_4$ and $R_5$, independently, are H, OH, $C_1$–$C_{18}$alkoxy, $NH_2$, NH—$R_6$ or $N(R_6)_2$ in which $R_6$ is $C_1$–$C_{18}$alkyl, $OR_6$ in which $R_6$ has its previous significance, phenyl, phenoxy or anilino, or pyrrolo, in which the respective phenyl, phenoxy or anilino, or pyrrolo moieties are optionally substituted by one, two or three substitutents selected from OH, carboxy, CO—$NH_2$, $C_1$–$C_{18}$alkyl or -alkoxy, $C_1$–$C_{18}$carboxyalkyl, $C_5$–$C_8$cycloalkyl, a methylidenecamphor group, a group —(CH=CH)$_m$C(=O)—$OR_6$ in which m is 0 or 1 and $R_6$ has its previous significance, or a group

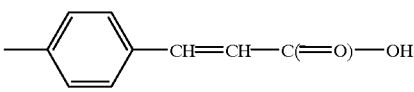

or the corresponding alkali metal, ammonium, mono-, di- or tri-$C_1$–$C_4$alkylammonium, mono-, di- or tri-$C_2$–$C_4$alkanolammonium salts, or the $C_1$–$C_{18}$alkyl esters thereof.

7. A method according to claim 6 in which the triazine compound is of the formula:

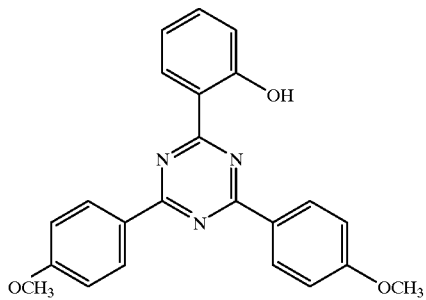
(3)
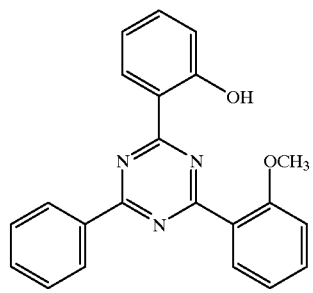
(4)
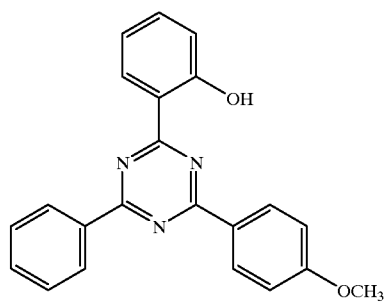
(5)
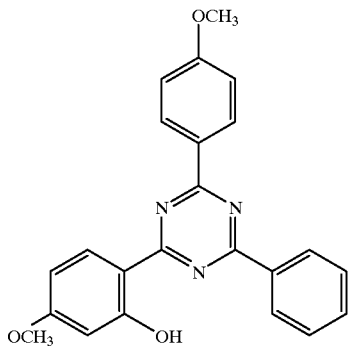
(6)
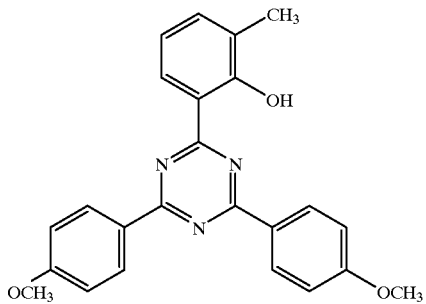
(7)

-continued
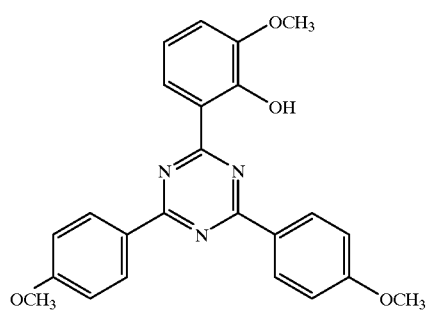
(8)
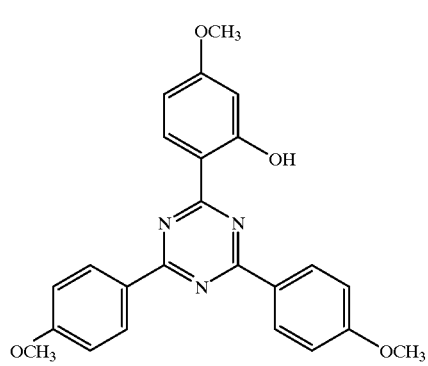
(9)
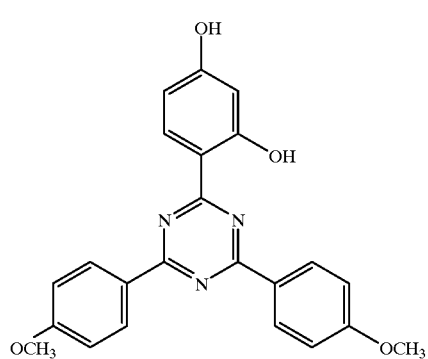
(10)
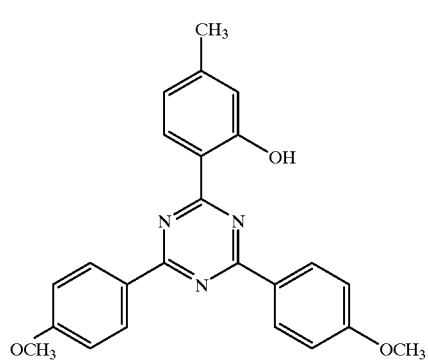
(11)

(12)
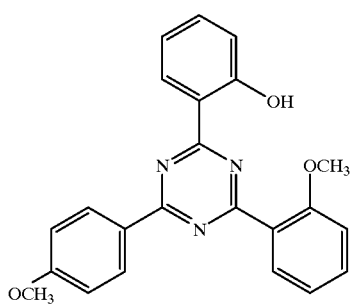
(13)
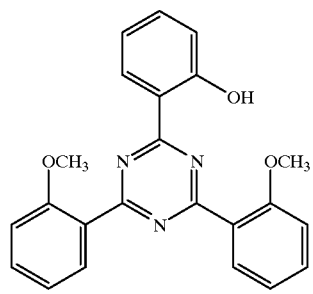
(14)
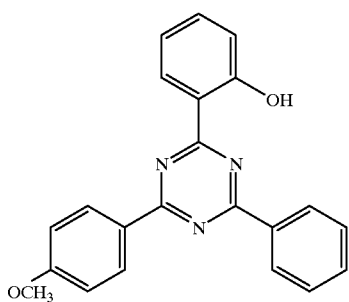
(15)
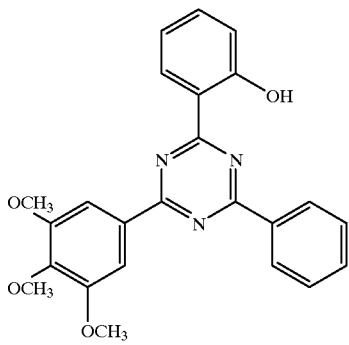
(16)
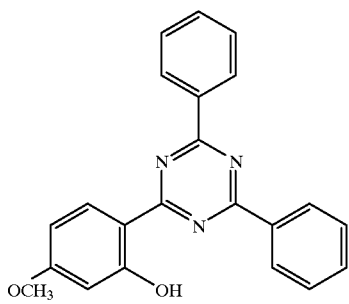

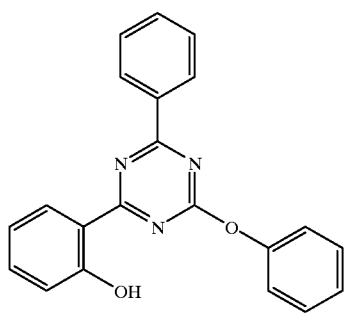
(17)
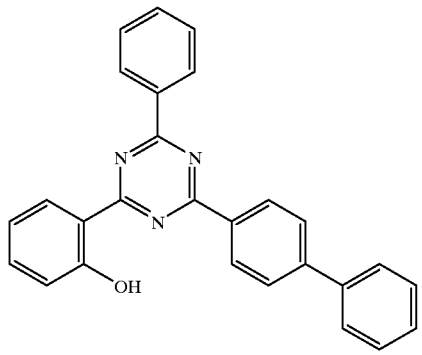
(18)
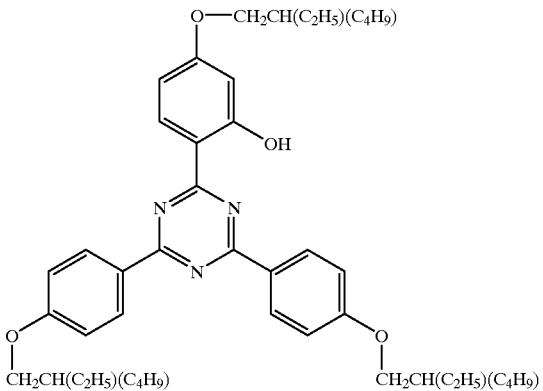
(19)
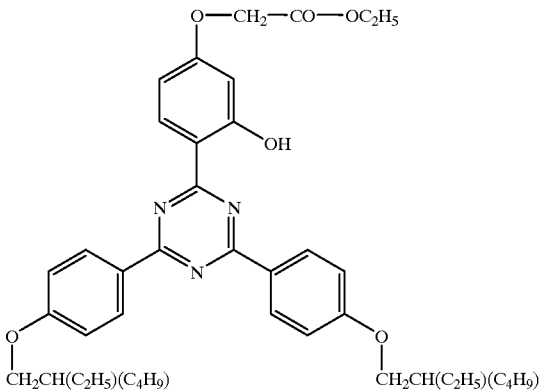
(20)

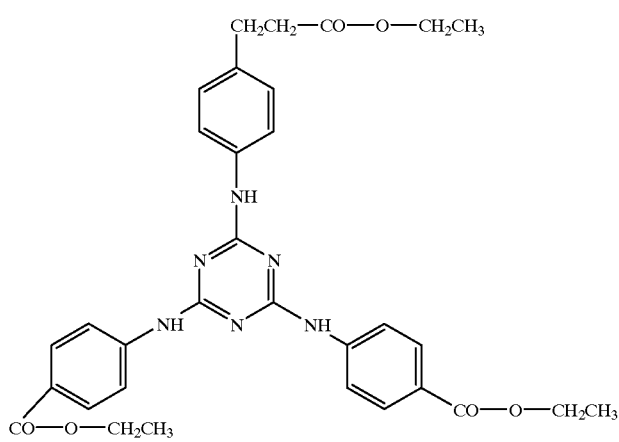
(21)
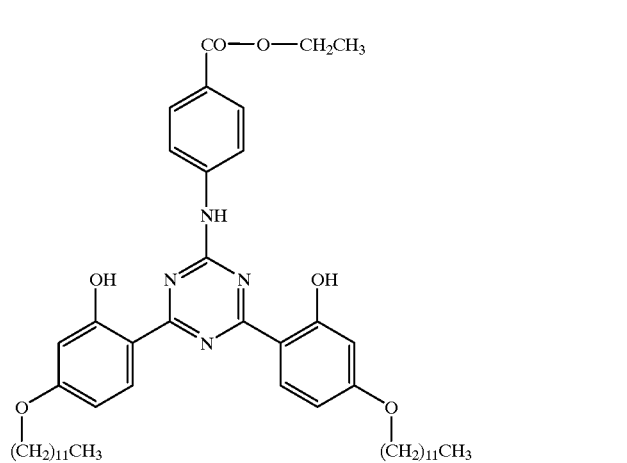
(22)
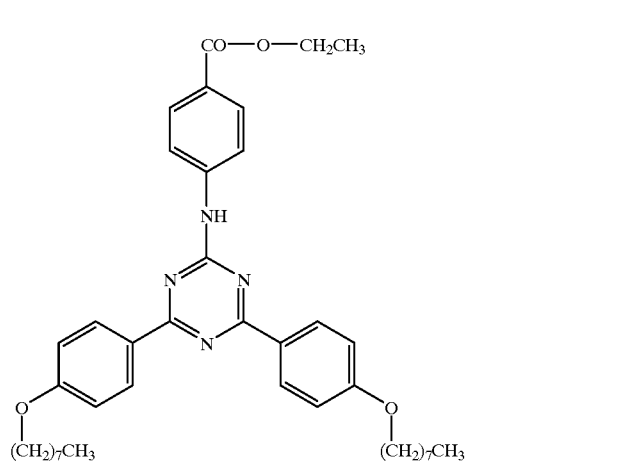
(23)

(24)
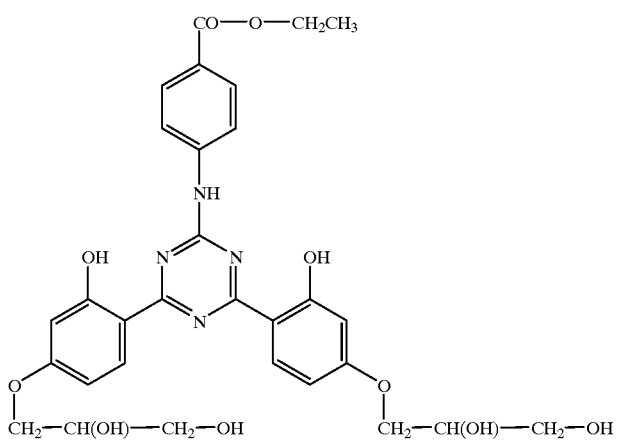
(25)
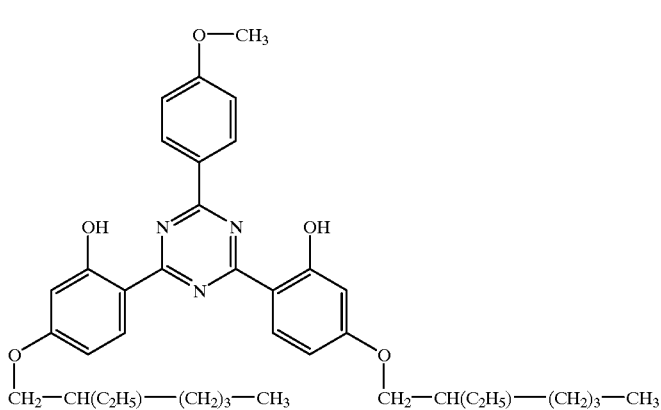
(26)
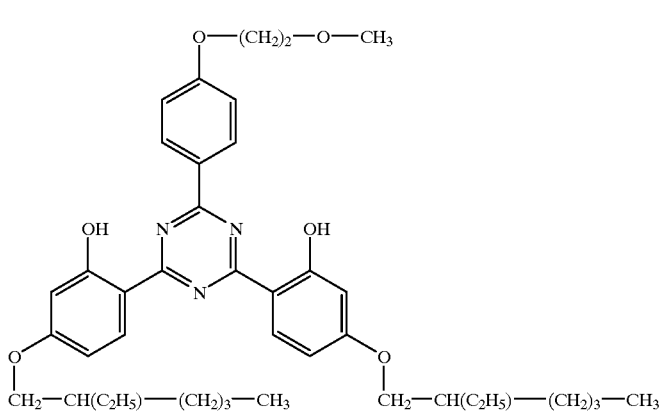
(27)
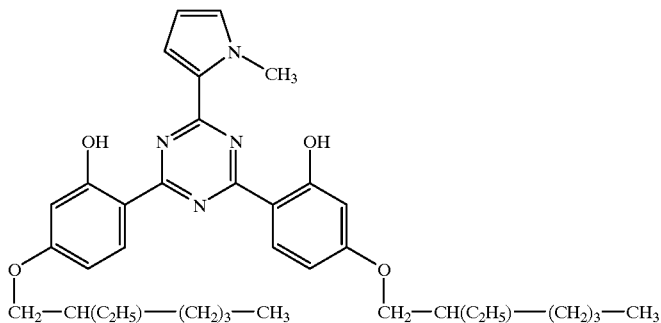

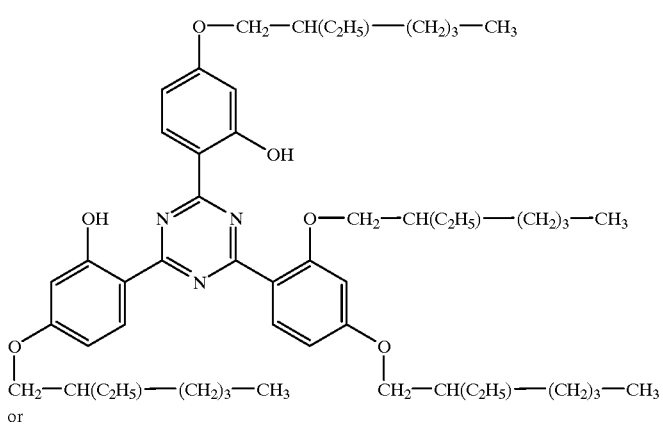
(28)

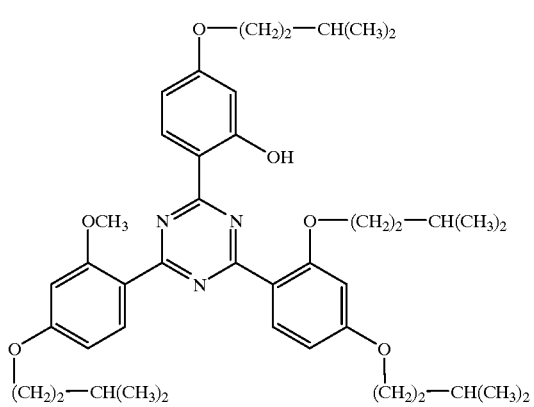
(29)

or is 2,4,6-tris(diisobutyl-4'-aminobenzalmalonate)-s-triazine or 2,4-bis(diisobutyl-4-aminobenzalmalonate)-6-(4'-aminobenzylidenecamphor)-s-triazine.

8. A method according to claim 6 in which the triazine compound has the formula:

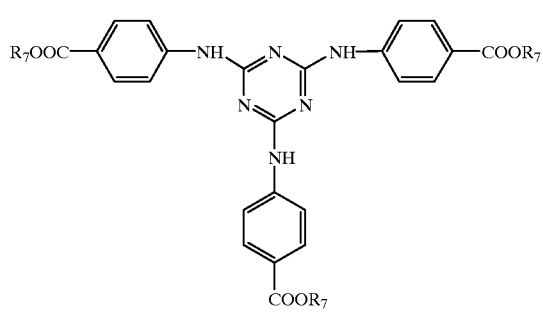
(30)

in which the individual radicals $R_7$ are the same or different and each is hydrogen; an alkali metal; an ammonium group $N(R_8)_4$ in which $R_8$ is hydrogen or an organic radical; $C_1$–$C_{20}$alkyl; or a polyoxyethylene radical which contains from 1 to 10 ethylene oxide units and the terminal OH group of which may be etherified by a $C_1$–$C_3$alcohol.

9. A method according to claim 8 in which when $R_7$ is an alkali metal it is potassium or sodium; when $R_7$ is a group $N(R_8)_4$ in which $R_8$ is as defined in claim 8, it is a mono-, di- or tri-$C_1$–$C_4$alkylammonium salt, a mono-, di- or tri-$C_2$–$C_4$alkanolammonium salt or a $C_1$–$C_{20}$alkyl ester thereof; when $R_8$ is a $C_1$–$C_{20}$alkyl group, it is a $C_6$–$C_{12}$alkyl group; and when $R_8$ is polyoxyethylene group, this contains from 2–6 ethylene oxide units.

10. A method according to claim 3 in which the triazole organic UV absorber has the formula:

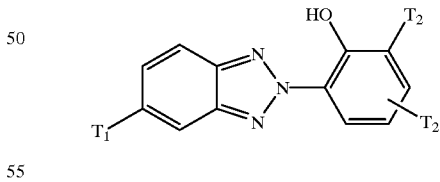
(31)

in which $T_1$ is $C_1$–$C_{18}$alkyl or hydrogen; and $T_2$ is $C_1$–$C_{18}$alkyl, optionally substituted by phenyl.

11. A method according to claim 10 in which $T_2$ is α,α-dimethylbenzyl.

12. A method according to claim 3 in which the triazole organic UV absorber has the formula:

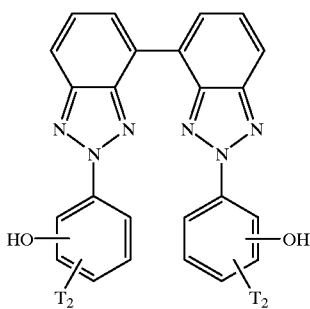

(32)

in which $T_2$ is $C_1$–$C_{18}$alkyl, optionally substituted by phenyl.

13. A method according to claim 3 in which the triazole organic UV absorber has the formula:

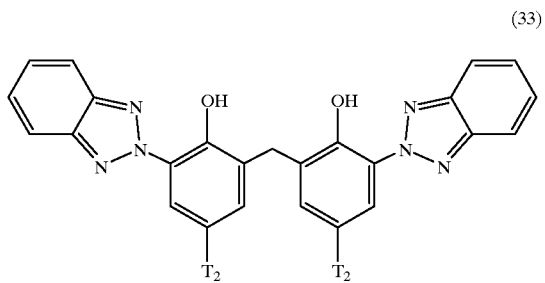

(33)

in which $T_2$ is $C_1$–$C_{18}$alkyl, optionally substituted by phenyl.

14. A method as defined in claim 13 in which $T_2$ is t-butyl.

15. A method according to claim 3 in which the vinyl group-containing amide organic UV absorber has the formula:

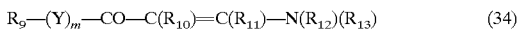

$$R_9-(Y)_m-CO-C(R_{10})=C(R_{11})-N(R_{12})(R_{13})$$ (34)

in which $R_9$ is $C_1$–$C_{18}$alkyl or phenyl optionally substituted by one, two or three substituents selected from OH, $C_1$–$C_{18}$alkyl, $C_1$–$C_{18}$alkoxy or CO—$OR_6$ in which $R_6$ is $C_1$–$C_{18}$alkyl; $R_{10}$, $R_{11}$, $R_{12}$ and $R_{13}$ are the same or different and each is $C_1$–$C_{18}$alkyl or hydrogen; Y is N or O; and m is 0 or 1.

16. A method according to claim 15 in which the compound of formula (34) is 4-octyl-3-penten-2-one, ethyl-3-octylamino-2-butenoate, 3-octylamino-1-phenyl-2-buten-1-one or 3-dodecylamino-1-phenyl-2-buten-1-one.

17. A method according to claim 3 in which the cinnamic acid amide organic UV absorber has the formula:

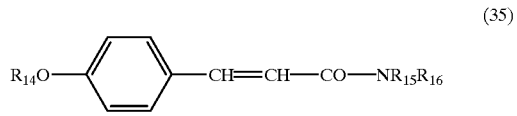

(35)

in which $R_{14}$ is hydroxy or $C_1$–$C_4$alkoxy; $R_{15}$ is hydrogen or $C_1$–$C_4$alkyl; and $R_{16}$ is —(CONH)$_m$-phenyl in which m is 0 or 1 and the phenyl group is optionally substituted by one, two or three substituents selected from OH, $C_1$–$C_{18}$alkyl, $C_{1-C18}$alkoxy or CO—$OR_6$ in which $R_6$ is $C_1$–$C_{18}$alkyl.

18. A method according to claim 17 in which $R_{16}$ is phenyl, 4-methoxyphenyl or the phenylaminocarbonyl group.

19. A method according to claim 3 in which the sulfonated benzimidazole organic UV absorber has the formula:

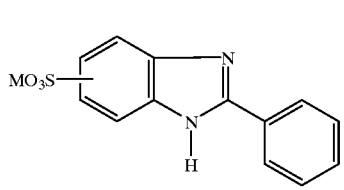

(36)

in which M is hydrogen or an alkali metal, an alkaline earth metal or zinc.

20. A method according to claim 1 in which the alkyl polyglucoside consists of a $C_1$–$C_{12}$ester of the compound of formula $C_nH_{2n+1}O(C_6H_{10}O_5)_xH$.

21. A method according to claim 20 in which the ester is formed by reacting formic, acetic, propionic, butyric, sulfosuccinic, citric or tartaric acid, with one or more free OH groups on the glucoside moiety ($C_6H_{10}O_5$).

22. A method according claim 1 in which the micronized insoluble organic UV absorber so obtained has a mean particle size in the range of from 0.01 to 2.0µ.

23. A method according claim 1 in which the micronized insoluble organic UV absorber has been produced by grinding it, in coarse particulate form, in a grinding apparatus, until the insoluble organic UV absorber has been converted into micronised form.

24. A method according to claim 23 in which the grinding apparatus is a jet, ball, vibration or hammer mill.

25. A composition comprising a micronised insoluble organic UV absorber produced by the method claimed in claim 1.

26. A sunscreen composition comprising a) 0.1 to 15% by weight of a micronized insoluble organic UV absorber composition according to claim 25; and optionally b) a cosmetically acceptable carrier.

27. A sunscreen composition according to claim 26 comprising a) 0.5 to 10% by weight of the micronised insoluble organic UV absorber composition; and optionally b) a cosmetically acceptable carrier.

28. A composition according to claim 26 in which the micronized insoluble organic UV absorber is an oxanilide a triazine, a triazole, a vinyl group-containing amide, a cinnamic acid amide or a sulfonated benzimidazole UV absorber.

29. A composition according to claims 26 in which the micronized insoluble organic UV absorber has a mean particle size in the range of form 0.01 to 2.0µ.

30. A composition according to claim 26 in which the micronized insoluble organic UV absorber has been produced by grinding it, in coarse particulate form, in a grinding apparatus, until the insoluble organic UV absorber has been converted into micronised form.

31. A composition according to claim 30 in which the grinding apparatus is a jet, ball, vibration or hammer mill.

32. A composition according to claim 26 in which the micronized insoluble organic UV absorber is used together with one or more further UV absorbers which are conventionally used in cosmetic compositions for the protection of human skin against UV radiation.

33. A sunscreen composition according to claim 26 which is formulated as a water-in oil or an oil-in-water dispersion, an oil or oil-alcohol lotion, a vesicular dispersion of an ionic or nonionic amphiphilic lipid, an oil-alcohol or alcohol gel, a solid stick or an aerosol formulation.

34. A sunscreen composition according to claim 33 which is formulated as a water-in oil or an oil-in-water dispersion and component b) comprises 5 to 50% of an oil phase, 5 to 20% of an emulsifier and 30 to 90% of water, each by weight based on the total weight of the carrier.

35. A sunscreen composition according to claim 34 in which the oil phase comprises one or more of a hydrocarbon oil, a wax, a natural oil, a silicone oil, a fatty acid ester or a fatty alcohol.

36. A sunscreen composition according to claim 34 in which the emulsifier comprises one or more of an ethoxylated ester of a natural oil derivative; a silicone oil emulsifier; an optionally ethoxylated fatty acid soap; an ethoxylated fatty alcohol; an optionally ethoxylated sorbitan ester; an ethoxylated fatty acid; or an ethoxylated glyceride.

37. A sunscreen composition according to claim 36 in which the ethoxylated ester of a natural oil derivative is a polyethoxylated ester of hydrogenated castor oil; and the silicone oil emulsifier is silicone polyol.

38. A sunscreen composition according to claim 26 in which the sunscreen composition also comprises one or more further components selected from the group consisting of emollients, skin moisturisers, skin tanning accelerators, antioxidants, emulsion stabilisers, thickening agents, moisture retention agents, film formers, preservatives, perfumes and colourants.

* * * * *